United States Patent

Luescher et al.

[11] Patent Number: 5,827,073
[45] Date of Patent: Oct. 27, 1998

[54] PHOTOREACTIVE PEPTIDE DERIVATIVES

[75] Inventors: Immanuel Luescher; Fabienee Anjuere; Andreas Layer; Pedro Romero; Jean-Charles Cerottini, all of Epalinges, Switzerland

[73] Assignee: Ludwig Institute for Cancer Research, New York, N.Y.

[21] Appl. No.: 498,461

[22] Filed: Jul. 5, 1995

[51] Int. Cl.$^6$ .......................... C07K 1/13; G01N 33/534; G01N 33/566

[52] U.S. Cl. ...................... 435/7.24; 435/68.1; 435/196; 436/501; 436/545; 530/345

[58] Field of Search .................. 435/7.24, 68.1; 436/501, 545; 530/345; 535/196

[56] References Cited

U.S. PATENT DOCUMENTS

5,405,940  4/1995  Boon et al. ............................. 530/328

OTHER PUBLICATIONS

Luescher et al., *J. Biol. Chem.*, 269:5574–5582 91994).
Romero et al., *J. Immunol. Methods*, 171:73–84 91994).
DiBrino et al., *J. Immunol.*,152:620–631 (1994).
Levine et al., *Tissue Antigens*, 44:174 (1994).
van der Bruggen et al., *Eur. J. Immunol.*, 24:2134 (1994).
Falk et al., *Immunogenetics*, 40:238 (1994).
Kubo et al., *J. Immunol.*, 152:3913 (1994).
Romero et al., *J. Exp. Med.*, 177:1247–1256 (1993).
Srivastava et al., *Adv. Cancer Res.*, 62:153 (1993).
Peitsch et al., *Int. Immunol.*, 5:233 (1993).
Luescher et al., *J. Immunol.*, 148:1003–1011 (1992).
Luescher et al., *Nature*, 351:72–74 (1991).
Tsomides et al., *Proc. Natl. Acad. Sci. USA*, 88:11276 (1991).
Townsend et al., *Ann. Rev. Immunol.*, 7:601 (1989).
Powers et al., *Int. J. Peptide Protein Res.*, 31:429–434 (1988).
Luescher et al., *Electrophoresis*, 8:508 (1987).
Tae et al., *Anal. Biochem.*, 121:286–289 (1982).
Brodsky et al., *J. Immunol.*, 128:129–135 (1982).
A. N. Eberle et al, *Meth. Enzymol.*, 109, 129–157, 1985.
V. E. Reyes et al, *Molec. Immunol.*, 28, 341–348, 1991.
D.C. Wraith et al, *Cell*, 59, 247–255, 1989.
F. Anjuere et al, *European Journal Of Immunology*, 25, 1535–1540, 1995.
F. Anjuere et al, *Analytical Biochemistry*, 229, 61–67, 1995.

*Primary Examiner*—David Saunders
*Attorney, Agent, or Firm*—Felfe & Lynch

[57] ABSTRACT

The invention relates to methods for making synthetic, photoreactive peptides and their use. A photoreactively labelled amino acid is incorporated into the peptide. The resulting peptide, when compared to the non-labelled form, is not impaired with respect to its ability to bind an MHC molecule.

14 Claims, 11 Drawing Sheets

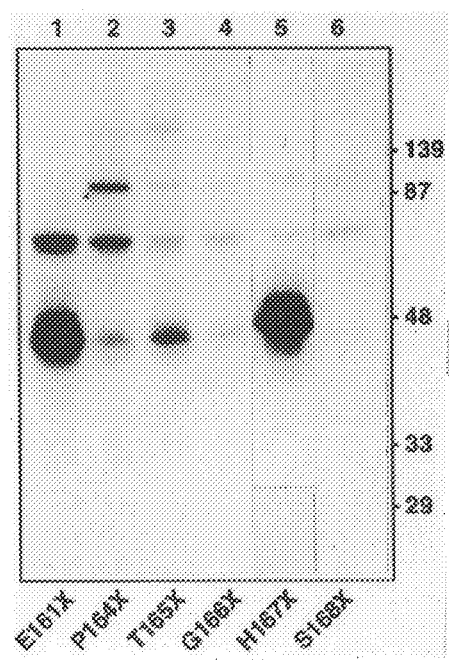

FIG. 5B

| Lane | Line | ws# | HLA-A | HLA-B | HLA-Cw |
|---|---|---|---|---|---|
| ① | BM 21 | 9043 | 1 | 4 | 0 |
| 2 | TAB089 | 9066 | 2 | 46 | 11 |
| 3 | JBUSH | 9035 | 32 | 38 | 12 |
| ④ | MOU | 9035 | 29 | 44 | 16 |
| 5 | TEM | 9057 | 26 | 38 | 12 |
| 6 | MZ070782 | 9002 | 24 | 14 | 2 |
| 7 | WT 8 | 9017 | 3 | 7 | 7 |
| 8 | WT 51 | 9029 | 23 | 65 | 8 |
| 9 | LBFU | 9048 | 30 | 13 | 6 |
| 10 | LEB.F | — | 33/2 | 14/12 | 8/? |
| ⑪ | LG2-EBV | — | 24/32 | 44/35 | 3/? |
| 12 | GALA | — | 2/28 | 35/72 | 2/? |
| 13 | DUR.A | — | 28/28 | 13/7 | ? |
| 14 | COS / Cw*1601 | — | — | — | *1601 |
| ⑮ | 807-02 | — | 24/29 | 7/39 | 7/? | ns

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Xaa is iodinated 2,
            3-[4- azidosalicyloyl]-diamino propionic acid ( x i ) SEQUENCE DESCRIPTION: SEQ ID NO: 1:

Glu Ala Asp Pro Thr Gly Xaa Ser Tyr
                            5

(2) INFORMATION FOR SEQ ID NO: 2:

(i) SEQUENCE CHARACTERISTICS:
        (A) LENGTH: 9 amino acids
        (B) TYPE: amino acid
        (D) TOPOLOGY: linear (ix) FEATURE:
        (D) OTHER INFORMATION: The Xaa following Gly is 2,
            3-[4- azidosalicyloyl]-diaminopropionic acid and the
            terminal Xaa is tyrosine dihydrogen phosphite (xi) SEQUENCE DESCRIPTION: SEQ ID NO: 2:

Glu Ala Asp Pro Thr Gly Xaa Ser Xaa
                            5

(2) INFORMATION FOR SEQ ID NO: 3:

(i) SEQUENCE CHARACTERISTICS:
        (A) LENGTH: 9 amino acids
        (B) TYPE: amino acid
        (D) TOPOLOGY: linear (ix) FEATURE:
        (D) OTHER INFORMATION: The Xaa following Gly is iodinated
            2, 3-[4- azidosalicyloyl]-diaminopropionic acid, and
            the terminal Xaa is tyrosine dihydrogen phosphite (xi) SEQUENCE DESCRIPTION: SEQ ID NO: 3:

Glu Ala Asp Pro Thr Gly Xaa Ser Xaa
                            5

(2) INFORMATION FOR SEQ ID NO: 4:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 4:

Glu Ala Asp Pro Thr Gly His Ser Tyr
                            5

(2) INFORMATION FOR SEQ ID NO: 5:

(i) SEQUENCE CHARACTERISTICS:
        (A) LENGTH: 10 amino acids
        (B) TYPE: amino acid
        (D) TOPOLOGY: linear (ix) FEATURE:
        (D) OTHER INFORMATION: The Xaa is iodinated 2,
            3-[4- azidosalicyloyl]-diaminopropionic acid.

(xi) SEQUENCE DESCRIPTION: SEQ ID NO: 5:

Xaa Glu Ala Asp Pro Thr Gly His Ser Tyr
                        5                   10

(2) INFORMATION FOR SEQ ID NO: 6:

(i) SEQUENCE CHARACTERISTICS:
        (A) LENGTH: 9 amino acids
        (B) TYPE: amino acid
        (D) TOPOLOGY: linear (ix) FEATURE:
        (D) OTHER INFORMATION: The Xaa is 2,3-[4-azidosalicyloyyl]
           - diaminopropionic acid ( x i ) SEQUENCE DESCRIPTION: SEQ ID NO: 6:

Glu Ala Asp Pro Thr Gly Xaa Ser Tyr
                      5

( 2 ) INFORMATION FOR SEQ ID NO: 7:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( D ) OTHER INFORMATION: Xaa is iodinated 2,3-[4-
            azidosalicyloyl]diaminopropionic acid ( x i ) SEQUENCE DESCRIPTION: SEQ ID NO: 7:

Glu Ala Asp Pro Thr Gly Xaa Ile
                      5

( 2 ) INFORMATION FOR SEQ ID NO: 8:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Xaa is iodinated 2,3-[4-
            azidosalicyloyl]diaminopropionic acid ( x i ) SEQUENCE DESCRIPTION: SEQ ID NO: 8:

Xaa Ala Asp Pro Thr Gly His Ser Tyr
                      5

( 2 ) INFORMATION FOR SEQ ID NO: 9:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO: 9:

Ser Ala Tyr Gly Glu Pro Arg Lys Leu
                      5

( 2 ) INFORMATION FOR SEQ ID NO: 10:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO: 10:

Glu Val Val Pro Ile Ser His Leu Tyr
                      5

( 2 ) INFORMATION FOR SEQ ID NO: 11:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO: 11:

Glu Val Asp Pro Ile Gly His Leu Tyr
                      5

(2) INFORMATION FOR SEQ ID NO: 12:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 12:

Glu Val Asp Pro Ala Ser Asn Thr Tyr
              5

(2) INFORMATION FOR SEQ ID NO: 13:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 13:

Glu Val Asp Pro Thr Ser Asn Thr Tyr
              5

(2) INFORMATION FOR SEQ ID NO: 14:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 14:

Glu Val Asp Pro Ile Gly His Val Tyr
              5

(2) INFORMATION FOR SEQ ID NO: 15:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 15:

Glu Val Val Arg Ile Gly His Leu Tyr
              5

(2) INFORMATION FOR SEQ ID NO: 16:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 16:

Tyr Met Asn Gly Thr Met Ser Asx Val
              5

PHOTOREACTIVE PEPTIDE DERIVATIVES

FIELD OF THE INVENTION

This invention relates to a method of making synthetic peptide derivatives which contain a radioiodinated photoreactive group. These peptide derivatives are useful for screening specific peptides for their ability to bind to specific MHC molecules.

BACKGROUND OF THE INVENTION

It is desirable to study molecular interactions, including interactions between macromolecular receptors, such as proteins, and low molecular weight ligands, such as peptides or nucleotides. One way to study such interactions is by photoaffinity labelling. Photoaffinity labelling pre-requires the synthesis of photoreactive ligand derivatives which bind to receptors in a manner which is identical or very similar to unmodified ligands. Upon photoactivation of the photoreactive groups, a covalent bond between the receptor and the ligand or peptide is formed. Inclusion of a radiolabel in the photoreactive group greatly facilitates the detection of the thus formed covalent receptor-ligand complex.

Photoaffinity labelling can be used to isolate and to identify receptors for known ligands, to map ligand contact sites on receptors, and to study the kinetics of receptor-ligand or receptor-peptide interactions. This technique is applicable on cell lysates and living cells, as well as with purified receptor-ligand systems.

One useful application of photoaffinity labelling concerns the study of peptide binding by MHC molecules. These molecules, which are expressed on cell surfaces, bind peptides to form antigenic MHC-peptide complexes. These complexes are recognized by cytotoxic T lymphocytes (CTL). This can result in the activation of CTLs (see Townsend et al., *Annu. Rev. Immunol.*, 7:601 (1989) and Romero et al., *J. Exp. Med.*, 177:1247–1256 (1993) and U.S. Pat. No. 5,405,940, which is incorporated herein by reference). Consequently, the formation of MHC molecule-peptide complexes is of great immunological interest.

The inventors have developed a novel method for synthesizing photoreactive peptide derivative which bind to and photoaffinity label MHC molecules. These photoreactive peptide derivatives can be used to assess the specific interactions of peptides with various MHC molecules.

SUMMARY OF THE INVENTION

This invention is directed to a method of producing synthetic photoreactive peptide derivatives. Synthetic peptides are synthesized by replacing an amino acid with a photoreactive group or amino acid, such as 2,3-[4-azidosalicyloyl]-diaminopropionic acid [DAP(ASA)], 4 azidophenacetyl thioester, 3 azidophenyl-3'-oxy-2-amino-L-propionic acid, or derivatives thereof. The resulting peptide derivatives are then radioiodinated. The photoreactive peptide derivatives are tested for their ability to bind to and photoaffinity label MHC molecules. Peptide derivatives which are able to bind and photoaffinity label MHC molecules can be used to screen various MHC molecules for crossreactivity and to screen various peptides for their ability to inhibit the photoaffinity labelling of a particular MHC molecule.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 2 is comprised of FIG. 2A, FIG. 2B and FIG. 2C.

FIG. 3 is comprised of FIG. 3A, FIG. 3B and FIG. 3C.

FIG. 4 represents HLA-A1 binding of photoreactive derivatives of MAGE-1 peptide Glu Ala Asp Pro Thr Gly His Ser Tyr (SEQ ID No: 4) as assessed by (i) a recognition based competition assay, and (ii) HLA-A1 photoaffinity labelling of transfected C1R cells;

FIG. 5 is comprised of FIG. 5A and FIG. 5B. FIG. 5B represents HLA class I molecule expression of the fifteen cell lines;

FIG. 6 is comprised of FIG. 6A and FIG. 6B. FIG. 7 is comprised of FIG. 7A and FIG. 7B.

DETAILED DESCRIPTION OF THE INVENTION

EXAMPLE 1

Figure 1:
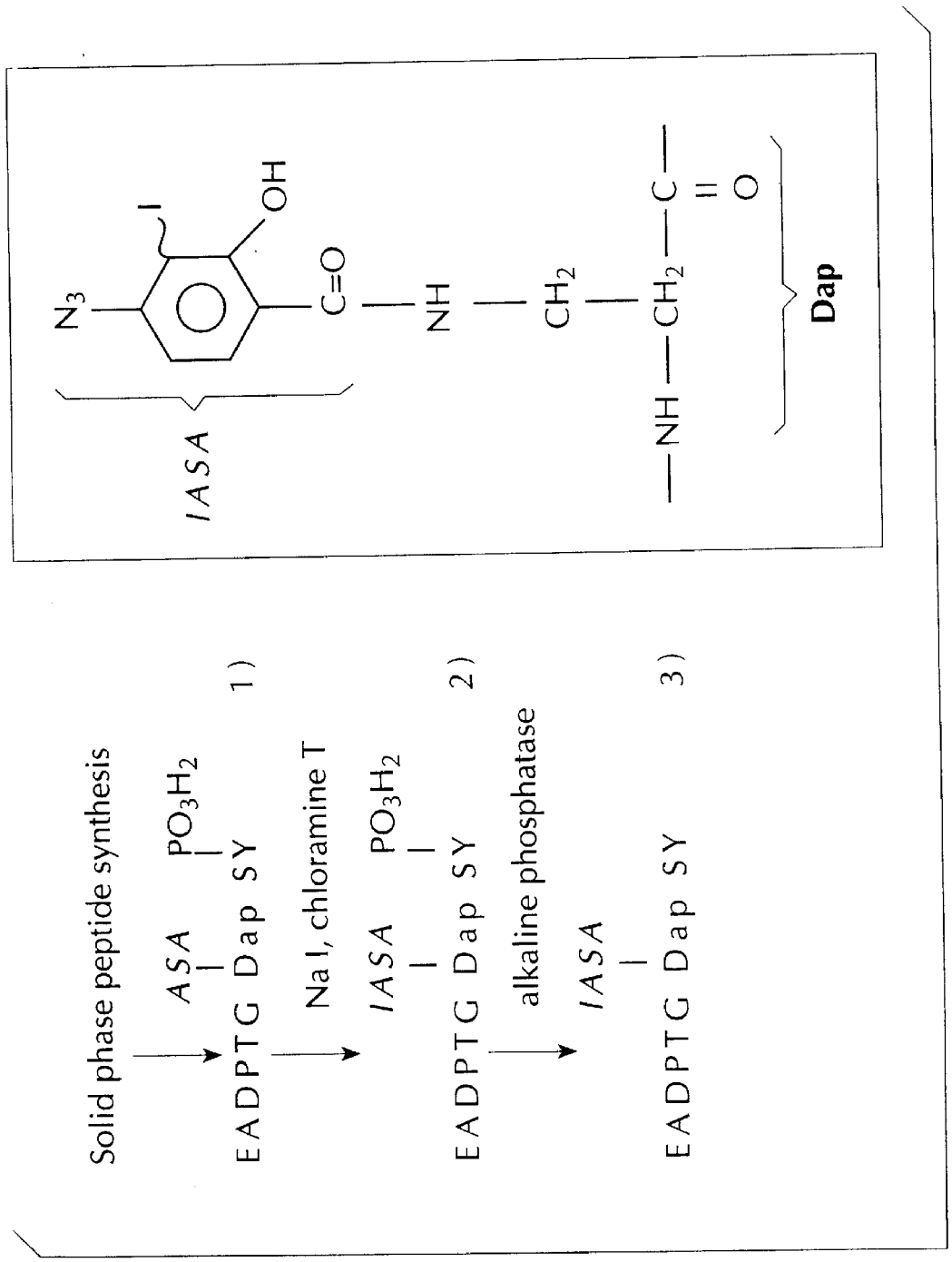
FIG. 1 represents the synthesis scheme of the photoreactive MAGE-1 peptide derivative Glu Ala Asp Pro Thr Gly Dap(IASA) Ser Tyr (SEQ ID NO: 1)

Synthesis of a photoreactive derivative of the melanoma derived MAGE-1 peptide 161–169, (EADPTGHSY) is described herein. This synthesis, which is schematically shown in FIG. 1, was performed in three steps. In the first step, a photoreactive derivative of the peptide EADPTGHSY was synthesized by replacing His-167 with the photoreactive amino acid Dap(ASA) . The C-terminal tyrosine was incorporated as phosphotyrosine. The resulting compound, SEQ ID NO: 2, was then subjected to iodination with sodium iodide and chloramine T. This iodination took place selectively at the ASA group because tyrosine iodination is prevented by the phosphate group. (If a synthetic peptide contains an amino acid which can be iodinated, that amino acid is attached to a phosphate group. This prevents the amino acid from iodinating. The phosphate group is removed after iodination is performed.) The main iodination product, SEQ ID NO: 3, was then dephosphorylated with alkaline phosphatase, which yielded the final product SEQ ID NO: 3.

SEQ ID NO: 2 was synthesized by conventional solid phase peptide synthesis based on the Fmoc strategy. The photoreactive amino acid Dap(ASA)—OH was introduced as Fmoc-Dap(ASA)—OH, which can be readily prepared from commercially available Fmoc-Dap(Boc)—OH by replacing the Boc group with ASA.

Fmoc-Dap (ASA)—OH was prepared from Nα-Fmoc, Nβ-Boc-L-2,3-diamino propionic acid (Fmoc-Dap(Boc)—OH) by replacing Boc with ASA. One gram (2.34 μMol) Fmoc-Dap(Boc)—OH was dissolved in 2 ml ice cold TFA containing 2% saturated aqueous phenol. After 1 hour of incubation at ambient temperature, the TFA was evaporated and dried Fmoc-Dap—OH was dissolved in 7 ml dimethylformamide and 480 μl of N,N-diisopropylethylamine. After adding 582 mg (2.1 μMol) of ASA-ONSu and 8 mg (60 μMol) of 1-hydroxybenzotriazole and stirring at ambient temperature for 2 hours, 100 ml of dichloromethane were added and the organic phase was extracted 3 times with 0.1 M KHSO$_4$ and 1 time with water.

Following drying over Na$_2$SO$_4$ and concentration to a volume of about 10 ml, the organic phase was neutralized with diisopropylethylamine. Upon adding 40 ml of diethylether, 866 mg (1.8 μMol) of Fmoc-Dap (ASA)—OH precipitated at −20° C. as a slightly yellow, crystalline material. As judged by C-18 HPLC (elution time 49 minutes, UV absorption maxima at 270 and 310 mm) and thin layer chromatography (Rf: 0,36 on silicagel-glass plates in chloroform/methanol: ⅔), the amino acid derivative was approximately 90% pure.

The peptide was deprotected and cleaved from the resin by treatment with trifluoroacetic acid/triisopropylsilane/water 90:5:5 for 2.5 hours at room temperature. After removal of the resin by filtration and evaporation of the trifluoroacetic acid, the crude product was reconstituted in 2 ml of 50% acetic acid and low molecular weight contaminations were removed by gel filtration on Sephadex G25 in 50% acetic acid. The materials eluted in the void volume were subjected to HPLC on an analytical C-18 column (4×250 μm, 5 μm particle size.

The column was eluted at a flow-rate of 1 ml/min by a linear gradient of acetonitrile on 0.01% trifluoroacetic acid in water, rinsing within one hour from 0 to 75%. The optical density of the eluate was monitored at 275 nm and UV absorption spectra of eluted materials were measured with an in-line 1000S diodearray spectrometer (ABI) connected to 286 AT computer. For processing of chromatograms and UV absorption spectra, the Lab-Calc software package (Galactic Industries Corp. Salem, N.H.) was used. For chromatography of radiolabelled materials the UV detector was by-passed and the chromatography was monitored by γ-counting of 3 μl aliquots of 0.75 minute fractions. The C-terminal tyrosine was introduced as Fmoc-Tyr(PO$_3$H$_2$)—OH by esterification to Wang resin.

Figure 2A:
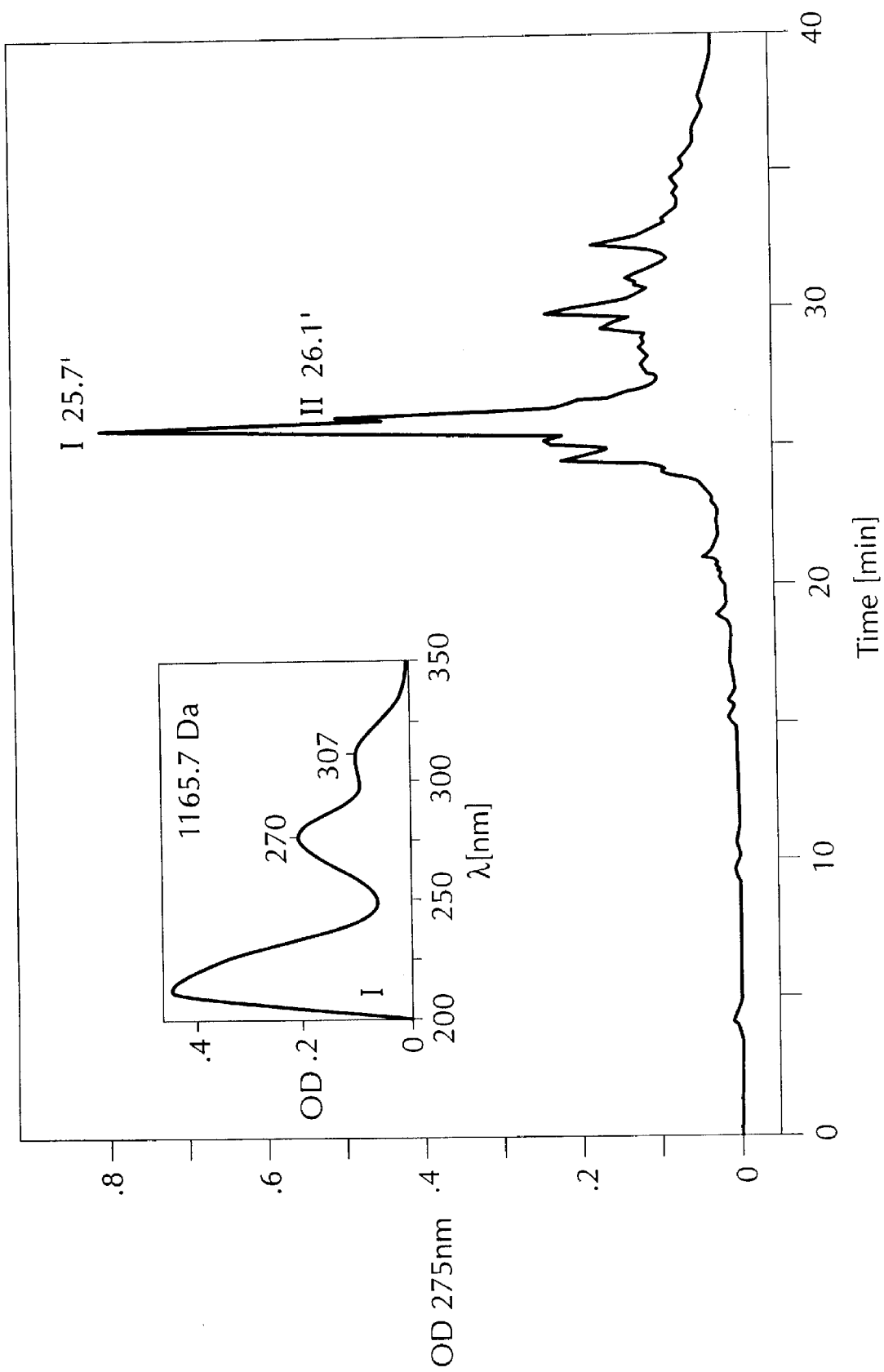
FIG. 2A represents HPLC analysis and characterization of Glu Ala Asp Pro Thr Gly Dap(Asa) Ser Tyr ($PO_3H_2$) (SEQ ID NO: 2)

FIG. 2A shows HPLC analysis of SEQ ID NO: 2 by measuring the OD at 275 nm. As shown in FIG. 2A, the main component eluted after 25.7 minutes (peak I), and displayed UV absorption maxima at 214, 270 and 310 nm (FIG. 2A insert) . These UV absorption maxima correspond to those previously observed for ASA-containing peptide derivatives. This material, as assessed by mass spectrometry, had a molecular mass of 1165.3 Da. This mass corresponds to the theoretical mass of SEQ ID NO: 2 (1165.7 Da, FIG. 2A insert). None of the other components observed in this chromatogram displayed the same UV absorption spectra or the same mass. The component eluting after 26.1 minutes (peak II) displayed the same UV absorption spectra as SEQ ID NO: 2, but had an incorrect mass of 1184.7 Da.

The HPLC purified SEQ ID NO: 3 was next subjected to iodination with sodium iodide and chloramine T. For non-radioactive iodination, 1 mg (0.85 μMol) of HPLC purified SEQ ID NO: 2 was reconstituted in 250 μl phosphate buffer (50 mM, pH 7.4) and mixed with an equimolar amount of aqueous sodium iodide (25.5 μl of a 5 mg/ml solution). Iodination was initiated by addition of 48.3 μl (1.06 μMol) of aqueous chloramine T (5 mg/ml). After mixing and incubation for 30 seconds, an equimolar amount of aqueous sodium bisulfate was added (22 μl of a 5 mg/ml solution) and the reaction mixture was subjected to HPLC.

Figure 2B:
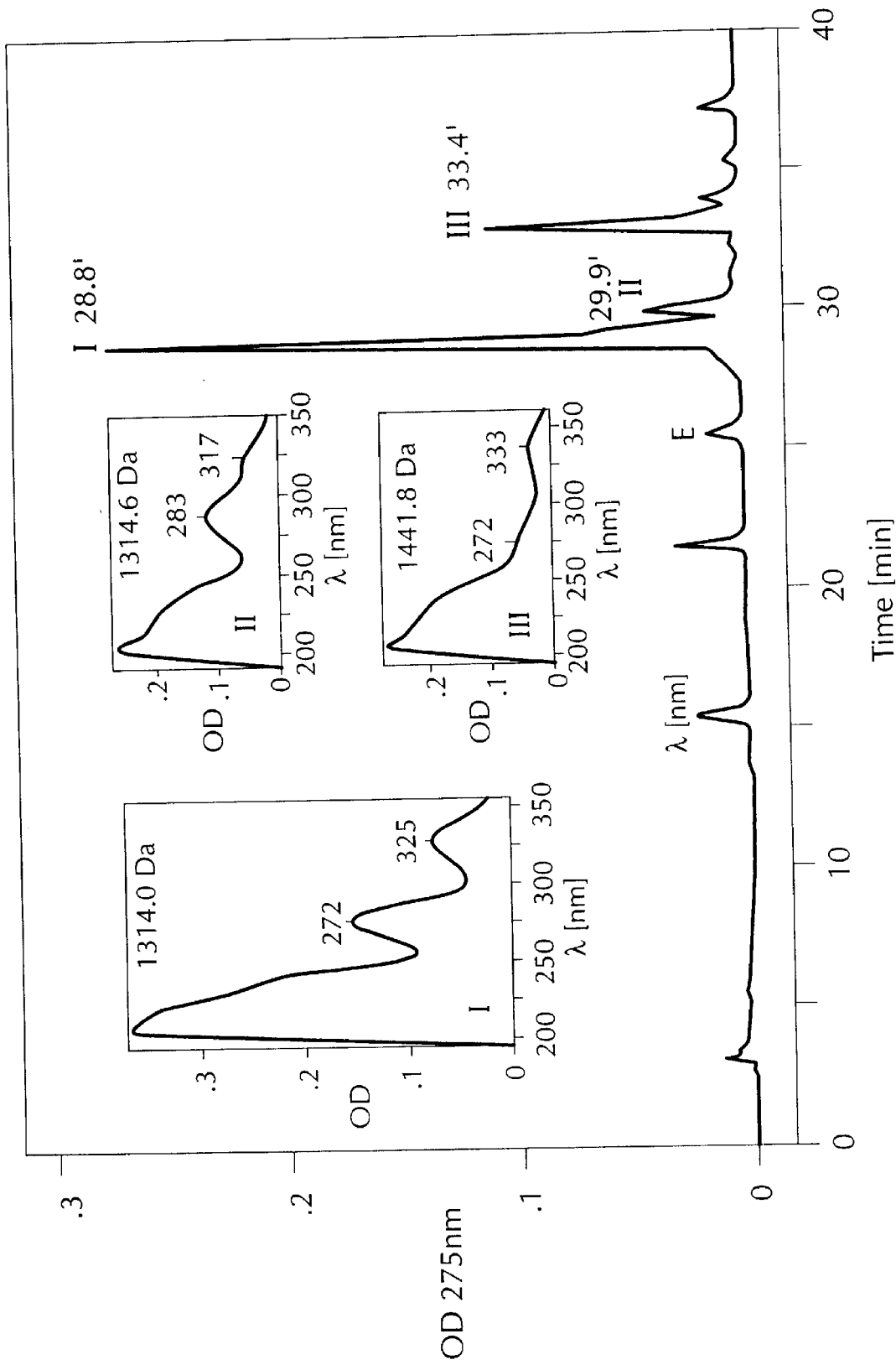
FIG. 2B represents HPLC analysis and characterization of Glu Ala Asp Pro Thr Gly Dap(IASA) Ser Tyr ($PO_3H_2$) (SEQ ID NO: 3)

FIG. 2B shows the HPLC analysis (OD 275 nm) and the UV absorption spectra of the iodination products labelled I, II and III. The corresponding UV absorption spectra and the observed masses are shown in the inserts I, II and III. The peak labelled E corresponds to unreacted SEQ ID NO: 2 and the main iodination product (peak I) corresponds to SEQ ID NO: 3

The main iodination product eluted from the HPLC column after 28.8 minutes (FIG. 2B, peak I) and displayed UV absorption maxima at 214, 272 and 325 nm (FIG. 2B, insert I). These UV absorption maxima are characteristic for amides of IASA (see Luescher et al., *J. Immunol.*, 148:1003–1011 (1992) and Luescher et al., *J. Biol. Chem.*, 269:5574–5582 (1994)), and likely correspond to the 3-iodo-4-azidosalicyloyl isomer (Tae et al., *Analytical Biochem.*, 121:286–289 (1982)). The mass observed for this iodination product was 1314.0 (FIG. 2B, insert I). The mass calculated for SEQ ID NO: 3 is 1291.2 Da, which is 22.8 Da lower than the observed mass. This difference in mass corresponds to sodium, which most likely, originating from sodium bisulfite used to stop the iodination reaction, formed a sodium hemi-phosphate. The minor iodination product eluting after 29.9 minutes (FIG. 2B, peak II) displayed UV absorption maxima at approximately 214, 283 and 317 nm and the same mass as SEQ ID NO: 3 and hence is likely to correspond to the 5-iodo-4-azido-salicyloyl isomer of SEQ ID NO:3 , which apparently is formed less well than the other IASA isomer.

Another iodination product eluted after 33.4 minutes (FIG. 2B, peak III) and displayed UV absorption maxima at 214, 272 and 332 nm, and a mass of 1443.2 Da (FIG. 2B, insert III). This product is most likely the 3,5-diiodo,4-azido salicyloyl derivative because the difference in the molecular mass between this material and SEQ ID NO: 3, 126.9 Da, corresponds to the mass of iodine. In addition, the delay in the elution from the HPLC column of this material is similar to the one observed between SEQ ID NO: 2 and SEQ ID NO: 3 (FIG. 2B, peak E, I and II), corresponding to the introduction of a hydrophobic iodine residue in the ASA group.

The IASA group was found to absorb in the same wavelength range as tyrosine and tyrosine phosphate, but have an over ten-fold higher molar extinction coefficient. All observed iodination products have different UV absorption spectra than SEQ ID NO: 2, which indicates that this iodination took place exclusively at the ASA group. In contrast, when the same iodination was performed on Glu Ala Asp Pro Thr Gly Xaa Ser Tyr (SEQ ID NO: 6), nearly 90% of the iodination took place at the tyrosine side chain, demonstrating that the phosphate group effectively prevents tyrosine iodination. This effect is most likely explained by steric hindrance and by a decrease of the electron density in the tyrosine side chain, as has been reported for tyrosine sulfates (Powers et al., *Int. J. Peptide Protein Res.,* 31:429–434 (1988)).

The HPLC purified compound EADPTGDap(IASA)SY ($PO_3H_2$) was dephosphorylated by treatment with alkaline phosphatase. EADPTGDap(IASA)SY($PO_3H_2$) was lyophilized and reconstituted in 500 µl of phosphatase digest buffer (0.1 M glycine, pH 10.4, containing 10 mM magnesium chloride and 10 mM zinc chloride) and 20 units of alkaline phosphatase (type VII-S) were added. After 5–10 minute incubation at room temperature the reaction mixture was subjected to HPLC.

Figure 2C:
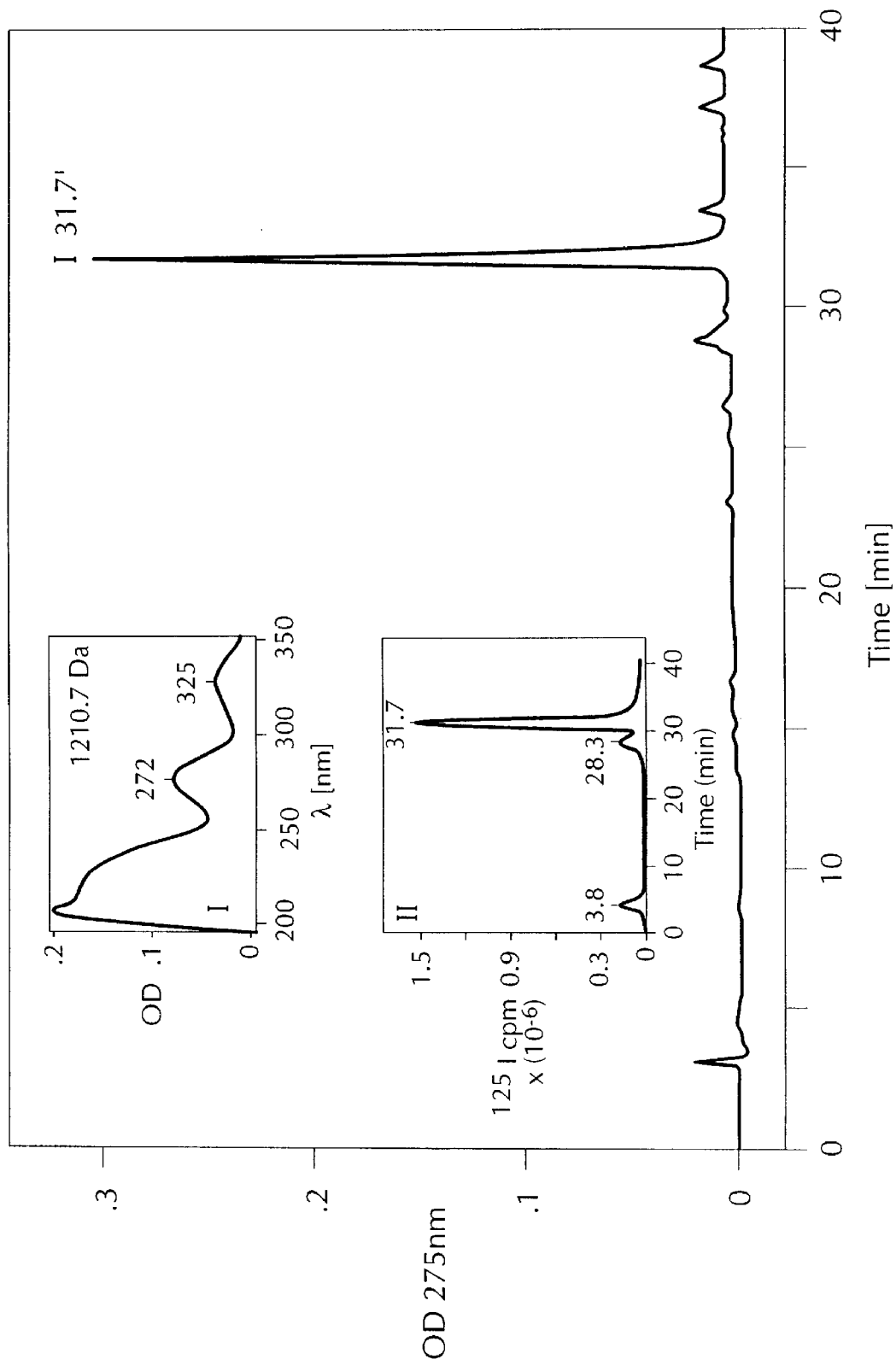
FIG. 2C represents HPLC analysis and characterization of SEQ ID NO: 1.

FIG. 2C shows HPLC analysis (OD 295 nm) and the UV absorption spectrum and the observed mass of the resulting final product, SEQ ID NO: 1 (FIG. 2C, peak I).

The main product eluted after 31.7 minutes, and displayed essentially the same UV absorption spectra as SEQ ID NO: 3, and a mass of 1212.9 Da (FIG. 2C, insert I). This mass correlates well with the calculated mass of SEQ ID NO: 1, (1212.7 Da), and the observed mass difference between SEQ ID NO: 3 and SEQ ID NO: 1 of 102 Da corresponds to the mass of mono-sodium phosphate. The dephosphorylation resulted in a delay of the elution from the HPLC column of about three minutes (FIG. 2B and FIG. 2C). This shift makes it possible to monitor the dephosphorylation by HPLC. Kinetic experiments showed that the dephosphorylation was already nearly complete (>95%) after 20 seconds of incubation. Similar results were obtained when other tyrosine phosphate containing peptides were treated the same, indicating that alkaline phosphatase is highly efficient in dephosphorylating tyrosine phosphorylated peptides.

Alternatively, SEQ ID NO: 2 was radioiodinated and the reaction mixture, following treatment with alkaline phosphatase, directly subjected to HPLC. The radioactivity of the column eluate was measured by γ-counting of 3 µl aliquotes (FIG. 2C, insert II). Typically, 10 µg of SEQ ID NO: 2 dissolved in 50 µl phosphate buffer (50 mM, pH 7.4) were mixed with 1 mCi of [$^{125}$I] sodium iodide. As discussed hereinabove, iodination was induced by adding 10 µl of chloramine T (5 mg/ml in water). After mixing and incubation for 30 seconds, 10 µl of sodium bisulfite (5 mg/ml in water) were added, followed directly by the same dephosphorylation and HPLC purification. The HPLC purified products were lyophilized and reconstituted in PBS at about $2.5 \times 10^8$ cpm/ml.

The yield of radioiodinations was typically more than 90% of the input iodine. Due to the high specific radioactivity of [$^{125}$I] iodine (approximately 2000 Ci/µMol), the ASA-peptide derivative subjected to iodination generally is in large excess relative to the iodine, and therefore the di-iodo product is not detectably formed (FIG. 2C, insert II). For this reason, in the case of radiosynthesis, the HPLC purification of SEQ ID NO: 3 can be omitted. In addition, the considerable delay in the elution from the reverse phase column makes possible complete separation of the iodinated peptide derivative from the uniodinated precursor. The HPLC purified mono-iodo derivative therefore has the same specific radioactivity as the iodine used for the iodination. While non-radioactive IASA-peptide derivatives can be stored frozen indefinitely, radioiodinated ones are prone to radiolysis, and therefore should be utilized preferentially within one week. These radioactive peptide derivatives are best stored at 2°–4° C. as PBS solutions of no more than $5 \times 10^8$ cpm/ml and vial.

EXAMPLE 2

The ability of the MAGE-1 peptide derivative SEQ ID NO: 1 to photoaffinity label HLA-A1 molecules was assessed by incubating HLA-A1 transfected C1R cells (C1R/A1) with the radiolabelled peptide derivative in the presence of β2-microglobulin at 26° C.

All photoaffinity labelling procedures were performed essentially as described by Luescher et al., *J. Immunol.,* 148:1003–011 (1992); Luescher et al., *Nature,* 351:72–74 (1991); Romero et al., *J. Exp. Med.,* 177:1247–1256 (1993); Luescher et al., *J. Biol. Chem.,* 269:5574–5592 (1994); and Romero et al., *J. Immunol. Methods,* 171:73–84 (1994). Briefly, HLA-A1 transfected C1R cells, cultured in hygromycin containing medium, or other cell types were resuspended in DMEM medium supplemented with 0.5% fetal calf serum, 10 mM HEPES and 0.25 µg/ml human β2-microglobulin, or as specified, at $6 \times 10^6$ cells/ml. One ml aliquotes were incubated in 6-well plates with $20 \times 10^6$ cpm of peptide derivative at 26° C. for 4 hours or as specified.

After UV irradiation with a 15 W mercury fluorescence lamp with an emission maximum at 365 nm and a band width of 80 nm for 4 minutes at a lamp-sample distance of 2 cm, the cells were washed 4 times with DMEM containing 2% calf serum and 1 time with PBS. The washed cells were lysed and boiled in reducing sample buffer supplemented with $MgCl_2$ and subjected to SDS-PAGE. Alternatively the UV irradiated samples were lysed with NP-40 detergent (0.7%) on ice in the presence of HEPES (50 mM), leupeptin (10 µg/ml), PMSF (0.1 mM), and iodoacetamide (10 MM). Immunoprecipitation of HLA molecules with immobilized W6/32 mAb (Brodsky et al., *J. Immunol.,* 128:129–135 (1982) and SDS-PAGE analysis of the immunoprecipitate were performed as described by Luescher et al., *Electrophoresis,* 8:508 (1987). The gels were evaluated by autoradiography and in some experiments by densitometry as described by Luescher et al., *J. Immunol.,* 148:1003–1011 (1992). Each labelling experiment was performed at least twice.

FIG. 3, lane 1 shows that the major radiolabelled material migrated with an apparent Mr of approximately 45 kDa. This material corresponds to the HLA-A1 heavy chain because it was immunoprecipitated with the W6/32 mAb, which binds all HLA class I molecules (FIG. 3, lane 2) and C1R/A1 cells significantly express only HLA-A1. This HLA-A1 photoaffinity labelling was completely inhibited in the presence of a 300 fold molar excess of the HLA-A1 restricted peptides MAGE-1 and MAGE-3 (FIG. 3, lanes 3 and 4). In contrast, no detectable inhibition was observed in the presence of the HLA-A2 restricted influenza matrix peptide 57–66 (FIG. 3, lane 5).

No detectable HLA labelling was observed when these photoaffinity labelling experiments were performed on the homozygous EBV transformed cell lines TEM and WT51, which express HLA-A26, B-38 and A23 and B65, respectively (FIG. 3, lanes 6 and 7). Equally negative experiments were obtained on eight other EBV cell lines expressing yet different HLA-A, B and C molecules, demonstrating that the photoaffinity labelling of HLA-A1 was allele-specific. This is in accordance with the observation that HLA-A1 binding peptides all express the HLA-Al binding motif, namely an acid residue in position three, usually a proline in position 4 and a tyrosine at the C-terminus.

Figure 3A:
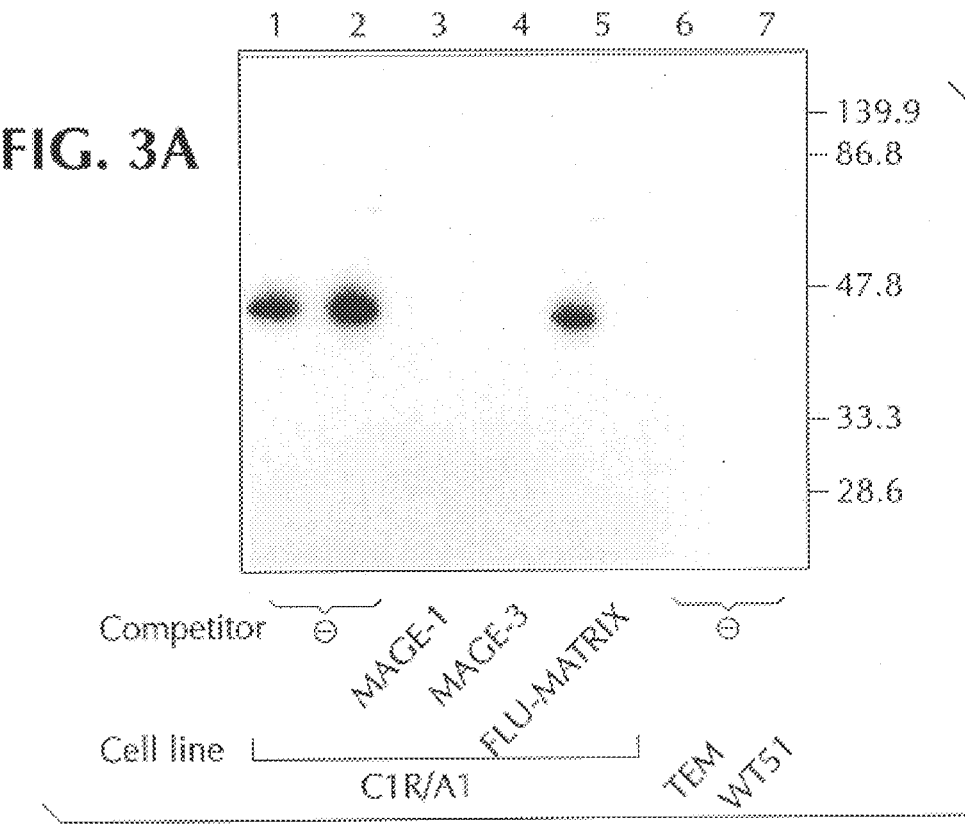
FIG. 3A represents SDS-PAGE analysis of EADPTGDap(IASA)SY incubated with C1R/A1 cells or WT51 cells in the presence of $\beta$2-microglobulin.
Figure 3B:
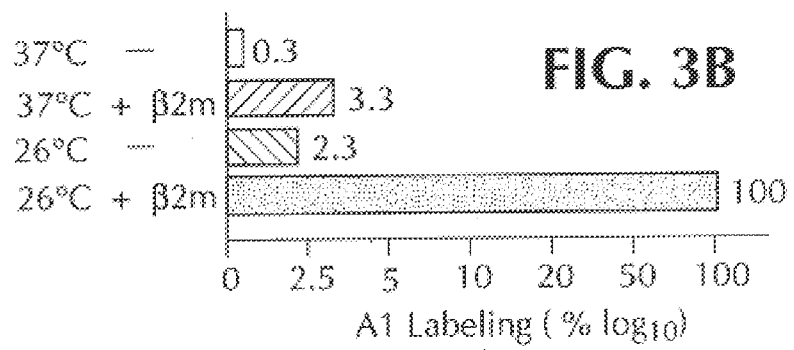
FIG. 3B represents SDS-PAGE where incubation was performed at 37° C. or 26° C. in the absence of presence of $\beta$2-microglobulin, and the autoradiograms were evaluated by densitometry.

Due to the remarkable specificity of this photoaffinity labelling and lack of significant labelling of other cellular components, this technique does not require the cumbersome isolation of MHC molecules (see FIG. 3A and Luescher et al., 1992, supra; Luescher et al., 1991, supra). It therefore allows for rapid testing of panels of peptides for their ability to bind to a given MHC class I molecule.

Alternatively, by testing panels of well-defined cell lines expressing different HLA class I molecule, this method can be used to assess the ability of a given peptide derivative to bind to other MHC class I molecules. Such screening cannot be readily performed by other techniques and is valuable in determining whether a given CTL epitope can also be presented in the context of MHC-molecules other than those previously known. For example, such experiments indicated that certain HLA-A1 binding MAGE peptides can also efficiently bind to HLA-A29, as described in further detail below.

This photoaffinity labelling approach can also be used for investigations of the molecular and cellular principles of peptide binding by cell-associated MHC class I molecules. Such studies, for example, showed that the binding of the MAGE-1 peptide derivative Glu Ala Asp Pro Thr Gly Xaa Ile (SEQ ID NO: 7) to C1R/A1-associated HLA-A1 molecules was significantly increased in the presence of excess exogenous human β2-microglobulin (3.3 fold) or at reduced temperature (2.3 fold) (see FIG. 3B). While both of these conditions have been previously reported to increase the binding of exogenous antigenic murine or human MHC class I molecules (see Romero et al., *J. Immunol. Methods,* 171:73–84 (1994)), it was surprising to observe that the combination of these conditions resulted in an over 300-fold increase in the peptide binding. This very substantial increase in the peptide binding was also found on EBV cell-lines (i.e., BM21 or GERL), and was nearly 20-fold higher than has been observed in the murine system (Romero et al., 1994, supra).

Figure 3C:
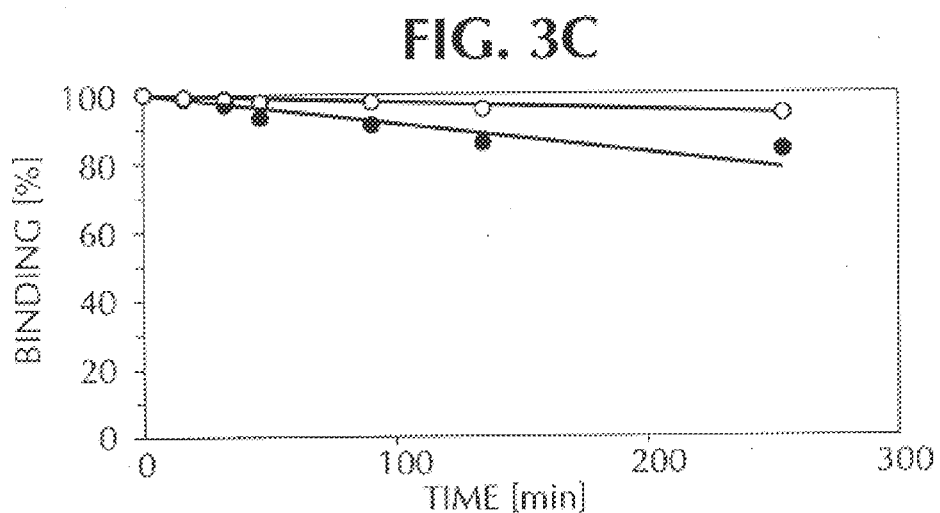
FIG. 3C shows the dissociation of HLA-A1 peptide derivative complexes on C1R/A1 cells either prior to or after UV irradiation.

This considerable increase is mainly accounted for by an accordingly less efficient peptide binding under physiological conditions (i.e., 37° C. and no exogenous β2-microglobulin) . Another difference between the human and murine system is the difference in the stability of MHC class 1-peptide complexes. On C1R/A1 cells, the dissociation of HLA-A1 peptide derivative complexes under physiological conditions was remarkably slow, and even after 6 hours of incubation less than 20% dissociation took place (FIG. 3C). Similarly slow dissociations have been reported for other HLA class I molecules (DiBrino et al., *J. Immunol.,* 152:620–631 (1994); Tsomides et al., Proc. Natl. Acad. Sci. USA, 88:11276 (1991)). In contrast, in the murine system, i.e., the $K_d$, $D_b$ of $L_d$ system, under these conditions rapid dissociations with halftimes in the range of one hour have been reported (Luescher et al., *Nature,* 351:72–74 (1991); Luescher et al., *J. Biol. Chem.,* 269:5574–5582 (1994); Romero et al., 1994, supra).

The procedures described herein are equally applicable for the synthesis either of non-radioactive photoreactive peptide derivatives or of non-photoreactive iodinated peptide derivatives. In the latter case the same procedures can be applied by using Nβ-salicyloyl-L-2,3-diaminopropionic acid instead of Dap(ASA). Due to the ease in which peptide derivatives can be synthesized in this way, it is easy to synthesize all possible Dap (IASA) derivatives of a given peptide. Testing the derivatives for their ability to photoaffinity label the restricting MHC class I molecule allows the identification of the peptide derivatives most suitable for photoaffinity labelling.

EXAMPLE 3

Several peptide derivatives, each having a photoreactive amino acid substitution at a different position, are prepared. All of the derivatives are then evaluated to determine which ones are suitable for MHC binding. Derivatives of the MAGE-1 peptide 161–169 (EADPTGHSY) were prepared as described in Example 1 by single amino acid substitution with photoreactive Dap(IASA) . As shown in FIG. 4A, all amino acids were substituted except the HLA-A1 contact residues Asp-163 and Tyr-169. The ability of these conjugates to bind to HLA-A1 was assessed in a recognition based competition assay. Labelling procedures were performed as described in Example 2.

To perform competition assays, $^{51}$Cr labelled C1R HLA-A1 transfected cells were incubated in the presence of a suboptimal concentration of the MAGE-3 peptide 168–176 with cloned HLA-A1-restricted MAGE-3-specific CTL 20/38. The concentration of the MAGE-1 161–169 peptide which resulted in 50% inhibition of the specific lysis was defined as 1, and the HLA-A1 competitor activities of the MAGE-1 peptide derivatives were expressed relative to this value. Alternatively, the radioiodinated peptide derivatives were incubated with HLA-A1 transfected C1R cells and following UV irradiation, the lysates of the washed cells were analyzed by SDS-PAGE (10%, reducing conditions).

Following incubation of these cells with the radioiodinated peptide derivatives and UV irradiation, cell lysates were analyzed by SDS-PAGE (FIG. 4B). The derivatives containing Dap(IASA) in position 1 or 7 efficiently labelled a material with an apparent Mr of approximately 45 kDa (lanes 1 and 5, respectively). The derivative containing Dap(IASA) in position 2 displayed reduced (100-fold) binding to HLA-A1, and was thus not further examined. The derivatives containing Dap(IASA) in position 4 or 5 weakly labelled this component, whereas the remaining two derivatives essentially failed to do so (lanes 2–4 and 5).

Different MAGE-1 peptide derivatives weakly labelled materials of apparent Mr of approximately 70, 96 and 150 kDa. It is possible that at least some of these materials are heat shock proteins, which have been reported to bind peptides (Srivastava et al., *Advances in Cancer Res.,* 62:153 (1993)). Since the different derivatives labelled these species with different intensities relative to HLA-A1, it is likely that the underlying binding principles are different.

EXAMPLE 4

The MAGE-1 peptide derivative Dap(IASA)-ADPTGHSY which efficiently bound to and photoaffinity labelled HLA-A1 was chosen to screen a panel of 14 lymphoblastoid B cell lines expressing over 44 different HLA-class I alleles.

FIG. 5B shows a summary of HLA class I molecule expression of the examined cell lines. The first 9 were HLA homozygous EBV transformed cells lines that have been described at the 10th International Histocompatibility Workshop (DuPont, *Immunobiology of HLA,* New York, Springer-Verlag, Vol. 1 (1987)). Workshop numbers are indicated as "ws#", and their HLA-C expression has been determined by PCR (Levine et al., *Tissue Antigens,* 44:174 (1994)). The heterozygous EBV transformed cell lines were derived from HLA-typed individuals. In the case of HLA-C, the serological typing was incomplete, as indicated by question marks. The remaining cell line was COS-7 cell transfected with HLA-Cw*1601. These cells were subjected to the same labelling procedure as described for FIG. 4B.

Figure 5A:
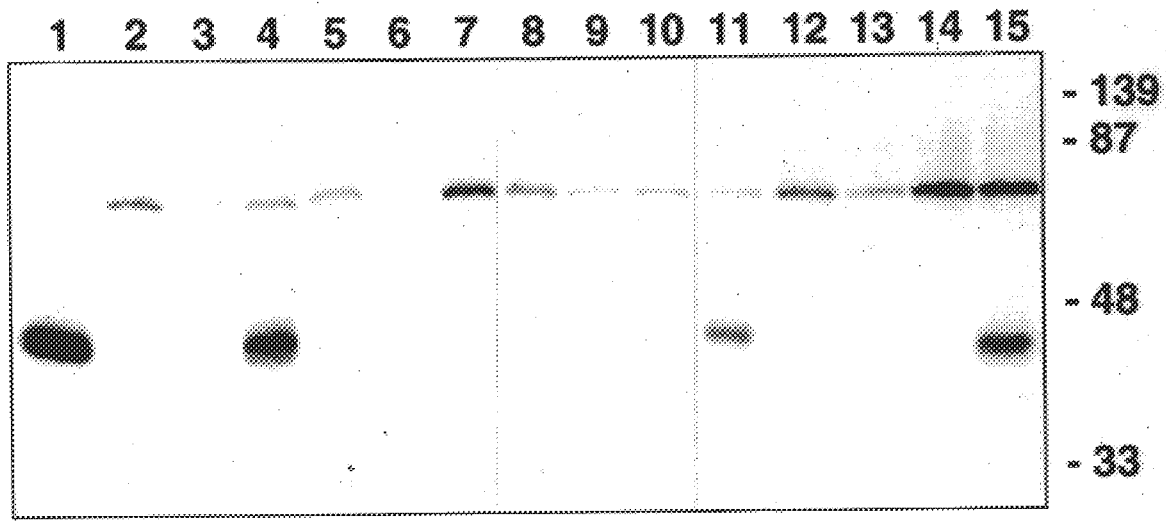
FIG. 5A represents photoaffinity labelling of fifteen different cell lines with the MAGE-1 peptide derivative Xaa Glu Ala Asp Pro Thr Gly His Ser Tyr (SEQ ID NO: 5).

As shown in FIG. 5A, significant photoaffinity labelling of a 45 kDa material was observed only in the case of the EBV transformed cell lines BM21 (lane 1), MOU (lane 4), LG2-EBV (lane 11) and 807-02 (lane 15). Labelling of this 45 kDa material was not detectable on the other lines tested (lanes 2, 3, 5–10, 12–14). This labelled material was immunoprecipitatable with W6/32 mAb and hence corresponds to HLA heavy chains.

The HLA photoaffinity labelling on BM21 cells, which expresses HLA-A1, was expected. However, the labelling observed on MOU cells, which express HLA-A*2902, HLA-B*4403 and HLA-C*601 (FIG. 2B), was very surprising. As suggested by the similarly efficient HLA labelling observed on the HLA-29+, HLA-B44 and HLA-Cw*1601 cell lines 807-02 (lane 15) and 806-04, this labelling involved mainly, if not exclusively, HLA-A29. HLA-Cw*1601 labelling could be ruled out, since COS-7 cells transfected with HLA-A1 or HLA-A29 (lane 14), but not with HLA-Cw*1601, displayed HLA labelling. This is consistent with the finding that an HLA-Cw*1601-restricted MAGE-1 peptide (SAYGEPRKL) displayed no homology with the HLA-Al binding MAGE peptides (see van der Bruggen et al., Eur. J. Immunol., 24:2134 (1994) and FIG. 6A). In caucasian populations the vast majority of HLA-A29 positive individuals express either HLA-A*2901 or HLA-A*2902. These two subtypes differ only by one amino acid in position 19 (His in HLA-A*2901 versus Asp in HLA-A*2902). Since this position is located in the last turn of the β pleated sheet, thus remote from the HLA-peptide binding domain, this amino acid substitution is unlikely to affect the peptide binding of HLA-A29.

The weak labelling observed on LG2-EBV cells (lane 11) suggests that Xaa Ala Asp Pro Thr Gly Ser Tyr (SEQ ID NO: 8) also binds to yet another HLA class I allele: possibly HLA-B44 or Cw3, which are not expressed on any of the cell lines that displayed no labelling, or another HLA-C allele that could not be typed by serology (FIG. 5).

EXAMPLE 5

Figure 6A:
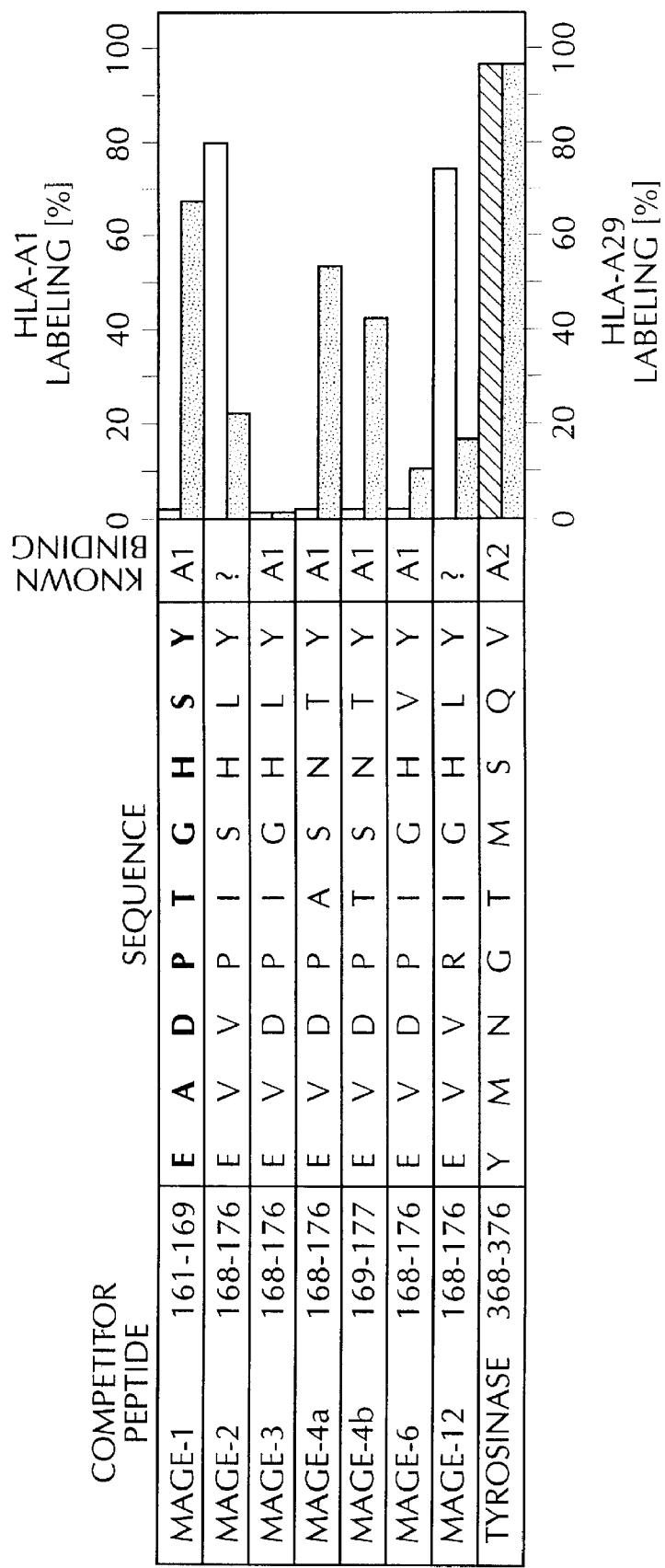
FIG. 6A shows the ability of MAGE encoded peptides to bind to HLA-A1 and HLA-A29 as assessed by inhibition of HLA-A1 and HLA-A29 photoaffinity labelling on C1R cells transfected with HLA-A1 and 807-02 cells, respectively.

HLA-A1 and HLA-A29 photoaffinity labelling was utilized to assess the ability of the MAGE peptides listed in FIG. 6A to bind to HLA-A1 and HLA-A29.

FIG. 6 shows binding of MAGE encoded peptides to HLA-A1 and HLA-A29. C1R cells transfected with HLA-A1 or 807-02 cells were incubated with Dap(IASA)-ADPTGHSY in the absence or presence of a 100-fold molar excess of the indicated peptides. After UV irradiation, the cells were lysed and the immunoprecipitated HLA molecules were analyzed by SDS-PAGE and the resulting autoradiograms were evaluated by densitometry. All experiments were performed at least in triplicate. Hundred percent labelling refers to the labelling observed in the absence of a competitor peptide (FIG. 6A).

The HLA-A1 photoaffinity labelling on C1R HLA-A1 transfectants was efficiently inhibited (about 98%) in the presence of a 100-fold molar excess of the MAGE-1, 3, 4a, 4b and 6 peptides. In contrast, the MAGE-2 and 12 peptides, which lack an acidic residue in position 3, were poor competitors. No significant inhibition was observed in the presence of the HLA-A2-restricted tyrosinase peptide 368–376 (van der Bruggen et al., 1994, supra). These results are in accordance with the known HLA-A1 binding motif, which has an acidic residue in position 3 and a C-terminal tyrosine (see Falk et al., Immunogenetics, 40:238 (1994); Kubo et al., J. Immunol., 152:3913 (1994); and DiBrino et al., 1994, supra). Moreover, the failure of the tyrosinase peptide to affect the HLA-A1 photoaffinity labelling demonstrated that under these conditions, the UV irradiation induced radicals do not detectably react with free peptide, as has been observed in other systems (see Luescher et al., Nature, 351:72 (1991); Luescher et al., J. Immunol., 48:1003 (1992); and Anjuere et al., Anal. Biochem.,In Press, 1995).

A different pattern of inhibition was observed in the HLA-A29 system (FIG. 6A). In the HLA-A29 system, the most efficient competitors were the MAGE-2, 3, 6 and 12 peptides, which at a 100-fold molar excess inhibited the HLA-A29 photoaffinity labelling on 807-02 cells by 80 to 90%. Conversely, the MAGE-1, 4a and 4b peptides inhibited HLA-A29 photoaffinity labelling only weakly (60–17%) and the tyrosinase peptide again displayed no detectable inhibition. The relatively inefficient inhibition of HLA-A29 photoaffinity labelling by the parental MAGE-1 peptide indicated that the substitution of Glu-161 with Dap (IASA) significantly increased its binding to HLA-A29. This may be explained by stabilizing interactions of the IASA group with this HLA molecule.

Figure 6B:
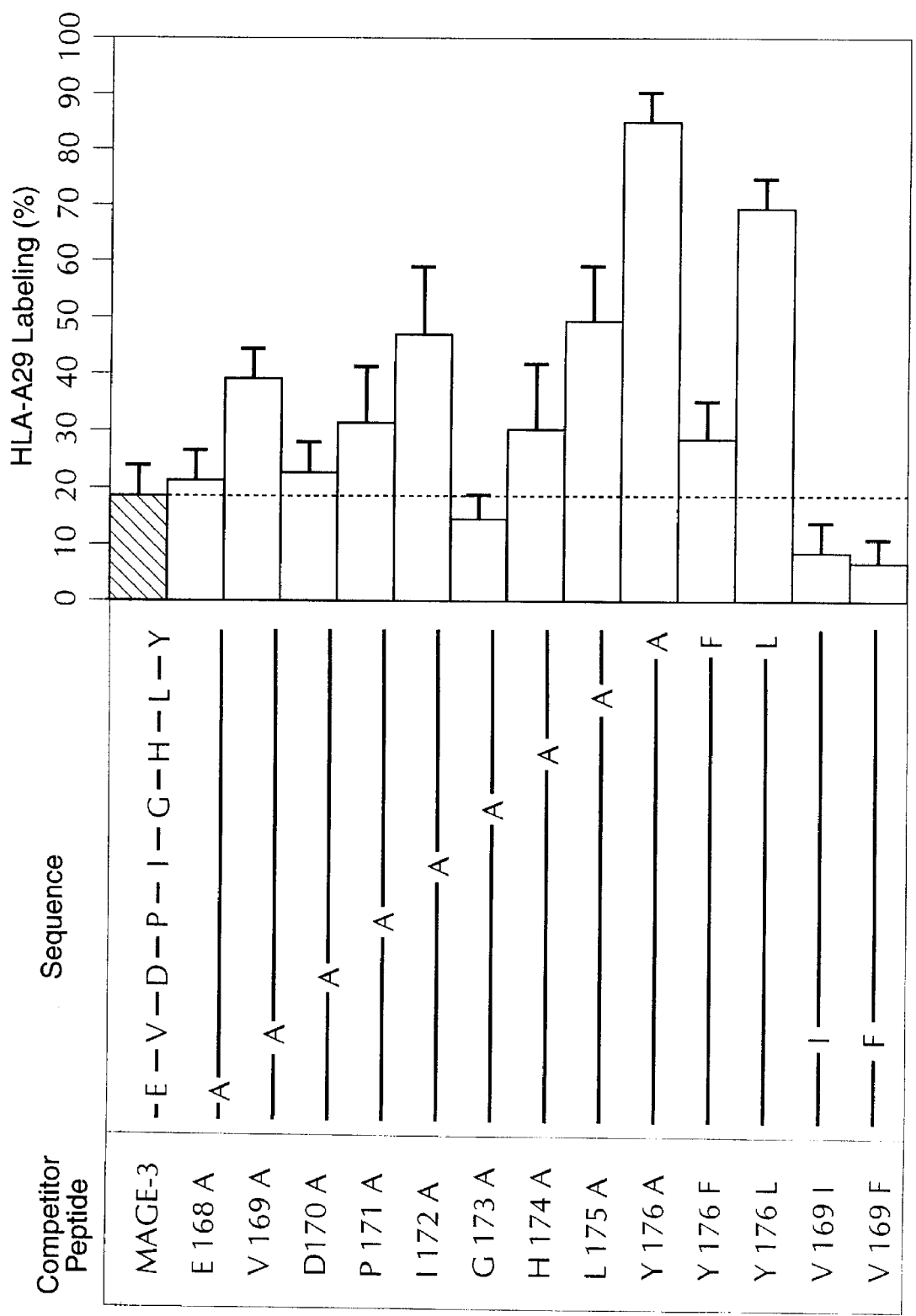
FIG. 6B represents a competition assay using MAGE-3 peptide variants as competitors.

To study in more detail the peptide binding by HLA-A29, the ability of single alanine substitute MAGE-3 peptide variants to bind to HLA-A29 was studied. As shown in FIG. 6B, HLA-A29 photoaffinity labelling was inhibited by approximately 80% in the presence of a 20-fold molar excess of the MAGE-3 peptide 168–176. In contrast, in the presence of the MAGE-3 variant containing Ala in position 9, the HLA-A29 photoaffinity labelling was inhibited by only 13%, indicating that the side chain of Tyr-176 was important for binding to HLA-A29. Replacing this tyrosine with phenylalanine, but not leucine, largely preserved the HLA-A29 competitor activity, indicating that for efficient HLA-A29 peptide binding, a C-terminal phenylalanine or a tyrosine is preferred, while an aliphatic hydrophobic residue per se is not sufficient. The other alanine substitutions that markedly reduced the binding of the MAGE-3 peptide to HLA-A29 were those of Ile-172, Leu-175 and, to a lesser degree, of Val-169. Alanine substitution of the other MAGE-3 peptide residues displayed no marked effects. These findings are in accordance with the observed differential ability of the different MAGE peptides to bind to HLA-A29. For example, the peptides MAGE-2, 3 and 6, which bind well to HLA-A29, all have an aliphatic residue in position 2, 5 and 8, whereas the MAGE-1 peptide, which binds poorly to this allele, has alanine in position 2 and polar residues in positions 5 and 8 (FIG. 6A).

EXAMPLE 6

To better understand peptide binding by HLA-A1 and HLA-A29 in molecular terms, models of their complexes with MAGE-3 peptide 168–176 were built.

In order to build these molecules, an average framework for the α1 and α2 domains of MHC class I molecules was constructed from structures currently available in the PDB database (HLA-A2, HLA-B27, HLA-Aw68 and H-2Kb). Models for the a α1 and α2 domains of other class I alleles were constructed from this framework using the ProMod knowledge-based modeling package (Peitsch et al., Int. Immunol., 5:233 (1993)). Briefly, a carbon-backbone was fitted onto the framework based on a primary sequence alignment optimized for 3D similarity. Loop regions were reconstructed by structural homology searches through the PDB databank, and missing side chains were rebuilt using a library of allowed rotamers. Similarly, an averaged framework for MHC-bound peptides was constructed from structures available from PDB, including the complexes of HLA-A2 with the peptides HIV gp 120 195–207, hepatitis B nucleocapsid 18–27, influenza A matrix protein 58–66, HIV reverse transcriptase 309–317 or HTLV-1 tax 11–and H-2K$^b$ with the peptides vesicular stomatitis virus nucleoprotein 52–59 or Sendai virus nucleoprotein 324–332. Peptides of interest were fitted onto this framework using ProMod.

The resulting crude models of MHC-peptide complexes were subjected to (1) rigid-body energy minimization, (2)

200 steps of Powell minimization with constrained a-carbons and (3) 200 steps of Powell minimization without constraints, using the X-PLOR package with the PARAM 11 parameter set. In order to assess peptide conformations with potentially lower free energies, the following molecular dynamics simulations were used: the peptide-MHC complex was heated to 300° C. in steps of 10° C., the peptide was allowed to move freely for 10 to 100 psec at this temperature and the complex was cooled again to 0° C. As before, the X-PLOR package and the PARAM 11 parameter data set was used. The final models were examined for consistency with known rules of peptide-MHC complex structure, such as hydrogen bonding, electrostatic interactions of the terminal amino and carboxyl groups of the peptide, and the presence of the canonical peptide binding pockets on the floor of the peptide-binding site.

Figure 7A:
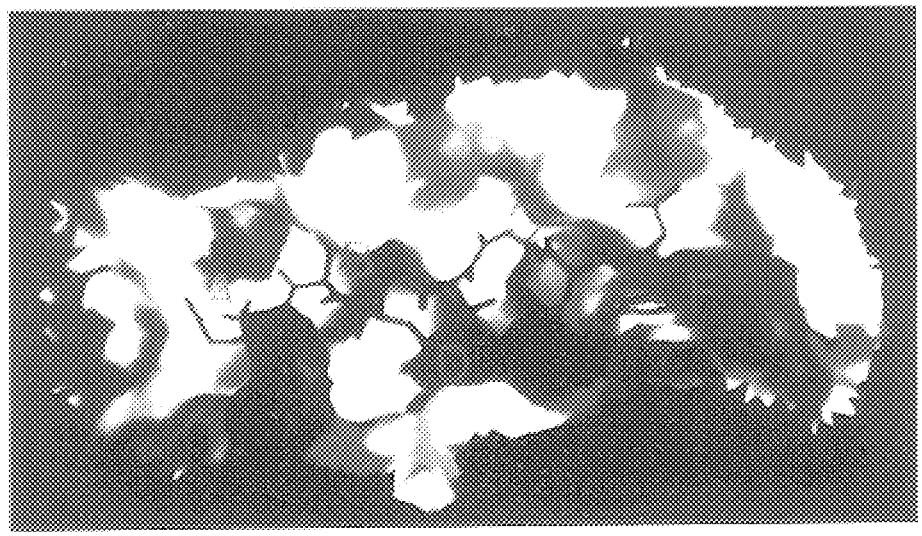
FIG. 7A represents molecular modeling of the HLA-A1-MAGE-3 complex.
Figure 7B:
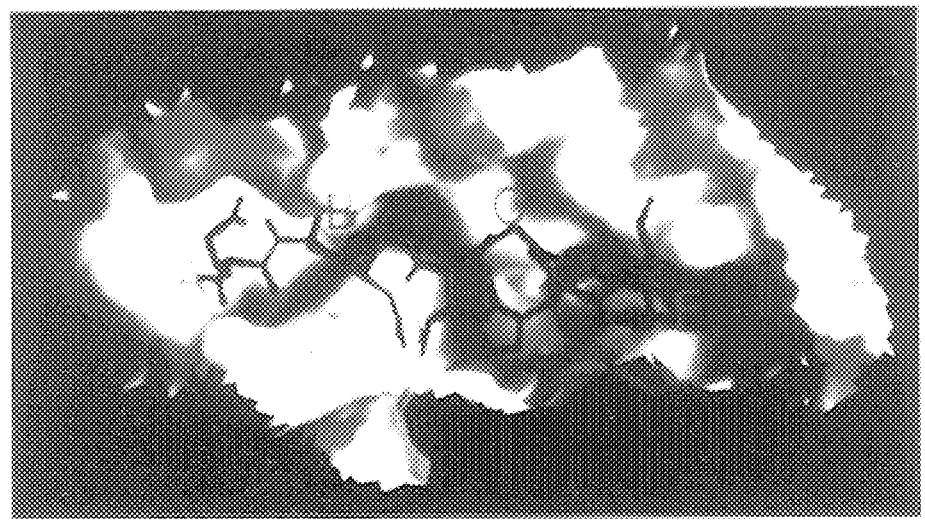
FIG. 7B represents the HLA-A29-MAGE-3 complex.

FIG. 7A shows molecular modeling of the HLA-A1-MAGE-3 peptide complex, and FIG. 7B shows molecular modeling of the HLA-A29-MAGE-3 eptide complex. The HLA peptide binding domains and adjacent regions are shown. The peptide carbon backbone is drawn in black. The capital letters indicate the locations of the different pockets of the peptide binding sites.

According to the model of the HLA-A1-MAGE-3 peptide complex, the main anchoring of the peptide involves the accommodation of the Asp-170 side chain in the D pocket and that of Tyr-176 in the F pocket of HLA-A1 (FIG. 7A). The former interaction involves the formation of a salt bridge between the side chains of peptide Asp-170 and Arg-114 of the floor of HLA-A1, whereas the latter involves II—II interactions of the peptide Tyr-176 side chain with Trp-147 of the HLA-A1 α2-helix and hydrogen bonding with Asp-116 of the floor of HLA-A1. These predictions are in agreement with the known peptide binding motif for HLA-A1 (Falk et al., 1994, supra; Kubro et al., 1994, supra; DiBrino et al., 1994, supra), and the observation that all of the MAGE peptides which have been tested, except for the MAGE-2 and MAGE-12 peptides, which lack Asp in position 3, efficiently bound to HLA-A1 (FIG. 6A). In addition, among the single alanine substitutions of the MAGE-3 peptide, only those of Asp-170 and Tyr-176 substantially impaired its binding to HLA-A1-A1.

On the other hand, modeling of the HLA-A29-MAGE-3 peptide complex suggests a significant different binding principle. As shown in FIG. 7B the geometry and physicochemical nature of the B and D pockets of HLA-A29 are very different than those of HLA-A1. According to the model, the hydrophobic B pocket accommodates the side chain of the valine in position 2. Peptide binding by HLA-A29 involves the accommodation of a hydrophobic peptide side chain in position 2 in a non-polar B pocket, which is consistent with the observation that the binding of the MAGE-3 peptide to HLA-A29 was impaired upon substitution in position 2 with alanine, but increased upon substitution with isoleucine or phenylalanine (FIG. 6B).

The model proposes an intimate binding of the peptide tyrosine side chain in the F pocket of HLA-A29. While this pocket is shallower than the one of HLA-A1, its binding of the peptide tyrosine side chain similarly involves, besides aromatic interactions with Trp-147, a stabilizing hydrogen bonding with Asp-74 of the a-helix of HLA-A29. This is consistent with the finding that replacement of the C-terminal peptide tyrosine with phenylalanine or with leucine considerably diminishes binding to HLA-A29 (FIG. 6B). The findings that isoleucine in position 5 and leucine in position 8 of the MAGE-3 peptide stabilized its binding to HLA-A29 (FIGS. 6A and 6B) are explained by the model by hydrophobic interactions of these side chains with equally hydrophobic domains on the corresponding flanking regions of the α2 and α1 helixes (FIG. 7B). The molecular modeling results agree with the finding that a single peptide can bind more than one HLA type.

HLA photoaffinity labelling on living cells can be used to assess peptide binding by different HLA class I molecules. A main finding of the present study is that the HLA-A1 binding MAGE-3 and 6 peptides as well as the homologous MAGE-2 and 12 peptides avidly bind to HLA-A29 and probably HLA-B44 or HLA-CW3. This suggests that these peptides may constitute epitopes recognized by HLA-A29, HLA-B44 or HLA-CW3 restricted MAGE specific CTL. Since the genes MAGE-2, 3 and 12 are the most frequently expressed MAGE genes in tumor samples, this will increase the proportion of patients eligible for immunotherapy with MAGE-encoded peptides.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method of producing a synthetic photoreactive peptide, comprising radioiodinating a peptide which contains a photo-reactively labelled amino acid selected from the group consisting of 2,3-[4-azidosalicyloyl]-diaminopropionic acid and 3-azidophenyl-3'-oxy-2-amino-L-propionic acid and derivatives thereof at said photoreactively labelled amino acid, said photoreactively labelled amino acid being positioned in said peptide such that said photoreactively labelled amino acid does not change the ability of said peptide to bind with a major histocompatibility (MHC) molecule.

2. The method of claim 1 wherein said radioiodinating is performed with iodide in the presence of chloramine T.

3. The method of claim 1 wherein said peptide is a MAGE-derived peptide.

4. The method of claim 3 wherein said peptide is selected from the group consisting of MAGE-1, MAGE-3, MAGE-4a, MAGE-4b, MAGE-6 and MAGE-12 derived peptides.

5. The method of claim 1 wherein said synthetic peptide contains an iodinatable amino acid, and wherein said iodinatable amino acid is attached to a phosphate group prior to performing said radioiodinating.

6. The method of claim 5 wherein said phosphate group is removed from said amino acid after performing said radioiodinating.

7. The method of claim 6 wherein said phosphate group is removed utilizing alkaline phosphatase.

8. A method for assessing ability of a peptide to bind to a major histocompatibility (MHC) molecule, comprising (i) preparing a derivative of said peptide which has a photoreactively labelled amino acid selected from the group consisting of 2,3-[4-azidosalicyloyl]-diamino propionic acid and 3-azidophenyl-3'-oxo-2-amino-L-propionic acid and derivatives thereof incorporated into the amino acid sequence of said peptide as a substitute for an amino acid in said peptide being assessed, wherein said photo-reactively labelled amino acid does not alter ability of said peptide to bind to an MHC molecule, (ii) radioiodinating said peptide at said photoreactively labelled amino acid, and (iii) determining ability of said derivative to bind to an MHC molecule as a determination of ability of said peptide to bind to said MHC molecule.

9. The method of claim 8 wherein said radioiodinating is performed with iodide in the presence of chloramine T.

10. The method of claim 8 wherein said peptide is a MAGE-derived peptide.

11. The method of claim 10 wherein said peptide is selected from the group consisting of MAGE-1, MAGE-3, MAGE-4a, MAGE-4b, MAGE-6 and MAGE-12 derived peptides.

12. The method of claim 8 wherein said synthetic peptide contains an iodinatable amino acid, and wherein said iodinatable amino acid is attached to a phosphate group prior to performing said radioiodinating.

13. The method of claim 12 wherein said phosphate group is removed from said amino acid after performing said radioiodinating.

14. The method of claim 13 wherein said phosphate group is removed utilizing alkaline phosphatase.

* * * * *

UNITED STATES PATENT AND TRADEMARK OFFICE
CERTIFICATE OF CORRECTION

PATENT NO. : 5,827,073
DATED : October 27, 1998
INVENTOR(S) : Luescher et al

It is certified that error appears in the above-indentified patent and that said Letters Patent is hereby corrected as shown below:

In the cover page, under the section entitled Other Publications, line 1, change "269: 5574-5582 91994)" to read as -- 269: 5574-5582 (1994) --.
In the cover page, under the section entitled Other Publications, line 2, change "171: 73-84 91994)" to read as -- 171: 73-84 (1994) --.

Signed and Sealed this

Third Day of April, 2001

Attest:

NICHOLAS P. GODICI

Attesting Officer     Acting Director of the United States Patent and Trademark Office